United States Patent [19]

Goldsberry

[11] Patent Number: Plant 6,554

[45] Date of Patent: Jan. 24, 1989

[54] DWARF CARNATION PLANT MAROON BELLS

[75] Inventor: Kenneth L. Goldsberry, Larimer, Colo.

[73] Assignee: Colorado State University Research Foundation, Fort Collins, Colo.

[21] Appl. No.: 45,455

[22] Filed: May 4, 1987

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Edwin L. Spangler, Jr.

[57] ABSTRACT

A carnation plant known by the cultivar name Maroon Bells was developed through a breeding program and is particularly characterized as to uniqueness by its dwarf growth habit and the following combined characteristics: upon pinching a rooted cutting, forms 4 to 6 lateral stems 18 to 25 cm long, each developing a terminal flower and 2 to 4 lateral buds which open intermittently after the terminal flowers senses; brilliant maroon flowers 3 to 5 cm in diameter with a slight spice fragrance; can be grown under specified environmental conditions either as a single pinched plant per 10 cm pot or 3 pinched plants per 13 cm pot, which results in an ideal new flowering house plant.

1 Drawing Sheet

My present invention relates to a new and distinct dwarf cultivar of *Dianthus caryophyllus* Linn. identified as plant 85-215-6 and given the name Maroon Bells.

Maroon Bells is a product of a breeding program started by me at Colorado State University in 1974, using commercially available semi dwarf germplasm, crossing selected unnamed seedlings and incorporating various known carnation germplasm with an objective of creating dwarf carnation cultivars that could be asexually produced for commercial use, in controlled environments, as flowering house plants. The goal was to produce a rooted vegetative shoot that, when placed in a 10 cm azalea pot would ultimately have the following characteristics: develop rapidly from a rotated cutting with 4 to 6 strong naturally formed vegetative breaks that would develop faster if the main leader was pinched 10 to 14 days after being placed in the pot. Upon flowering, 12 to 14 weeks following a winter pinch, have a total height, including the pot, of 22 to 25 cm with a 33 to 50 mm flower and an abundance of buds on each reproductive shoot, which would continue to open over a period of 3 to 4 weeks in most home environments. Plants with typical blue-grey carnation foliage and flowers with a degree of clove fragrance, were also desirable characterstics.

Maroon Bells were originated from a cross made in a controlled breeding program at the Horticulture Department, W. D. Holley Plant Environmental Research Center, Colorado State University, Fort Collins, Colo. using the unnamed seed parent 83-15-20 and an unnamed pollen parent 82-43A, also developed by the present inventor.

Maroon Bells was discovered and selected as one flowering plant within the progeny of the stated cross by Kenneth L. Goldsberry on June 24, 1985 in a controlled environment in Fort Collins, Colo.

The first act of asexual reproduction of Maroon Bells was accomplished when vegetative cutting's were taken, by the inventor, from the initial selection on Sept. 5, 1985 in a controlled environment in Fort Collins, Colo. The initial rooting of the cuttings and performance of the resulting plants has demonstrated that the distinctive characteristics of this new cultivar Maroon Bells, here in disclosed, appear to be firmly fixed and hold true from generation to generation.

Maroon Bells has not been observed under all possible environmental conditions. The phenotype may vary significantly with variation in the production environment including irrigation regimes, temperature, light intensity, day length and nutritional programs. It has been observed and evaluated, from a rooted cutting to a mature plant while being grown in Fort Collins and Denver, Colo. and Encintias and Salinas, Calif. under greenhouse conditions, which approximate those generally used in commercial practice.

The following traits, which have been repeatedly observed, characterize Maroon Bells and distinguishes it as a new and distinct dwarf carnation cultivar:

1. Somatic chromosome is 2n=30.
2. A double type flower, similar to commercial cut flower spray types.
3. Flower size ranges from 46 to 57 mm in diameter
4. Maroon flower color.
5. Medium flowering response on a scale of early, medium or late flowering.
6. Four to six lateral shoots develop following a pinch of the main stem.
7. Two or 3 flowers and buds showing color on each flowering stem. As the old flowers senese, the lateral buds continue to open.
8. Peduncle length on a single stem varies between 2 to 3.5 cm.
9. Plant height ranges between 18 to 25 cm.
10. Slight spice fragrance.

There are no dwarf carnation cultivars, for house plant use, presently developed and known to the inventor.

The accompanying colored photographs taken on Oct. 26, 1986, using an 18 percent Kodak photographic gray card as a color base, illustrate in perspective view and the overall appearance of Maroon Bells (85-215-6) grown in 10 cm (single plant) and 15 cm (3 plants) azalea pots. The buds, inflorescence, stem, foliage characteristics and color of Maroon Bells are typical and true as possible with illustrations of this type.

The following detailed description of my new dwarf carnation cultivar are based upon observations of greenhouse grown plants made in 1986 at Fort Collins, Colo. The color values were determined in a standard color viewing booth with a 5000° K. fluorescent light source using references developed and published by The Royal Horticultural Society, London, England.

PLANT CHARACTERISTICS

Origin: Seedling selection.

Parentage:

*Seed parent.*—Selected unnamed seedling, 83-15-20 (Goldsberry).

*Pollen parent.*—Selected unnamed seedling 82A-43A (Goldsberry).

Classification:

*Botanic.*—*Dianthus caryophyllus* Linn. cv. Maroon Bells.

*Commercial.*—Dwarf carnation for pot plant production.

Propagation: Vegetative cuttings, 6 to 8 cm. in length initiate visible roots in 8 to 10 days in the winter and 5 to 8 during the summer, when rooted under mist in a rooting medium temperature of 20° C. A quality rooted cutting with an abundance of roots, is usually ready to plant in 15 days in the summer and 18 to 20 in the winter.

Growth habit: Four to six lateral shoots form naturally, but are accelerated by removing the terminal portion of the main stem, at the sixth or seventh node from the top, resulting in a compact, bushy and strong up right plant. Some basal branches may elongate enough to place apical buds on a plane 2–5 cm above the terminal flowers of the initial stems.

Stems: Numerous lateral branches form close to the base of the plant and vary in length from 18–25 cm, having 8 to 11 nodes with opposite leaves. A reproductive bud usually forms at each upper 3 to 5 nodes. Shoots forming at the sixth or seventh node below the terminal flower, usually develop into another flower stem in proper environmental conditions. All stems have a blue-grey glaucous condition, approximating 189B in color.

Foliage: Leaves are abundant and typical of the commercial carnation type. The leaves at the fifth and sixth nodes from the top of each stem range in length from 10.2 to 12.7 cm and have an average width of 9.3 mm., but are progressively smaller above and below these nodes. Both the upper and lower sides of the leaves are dark green and have a blue-grey glaucous condition. The color of both surfaces is identified as 189B with the surface bloom present and 189A when it is removed.

INFLORESCENCE CHARACTERISTICS

Buds: Terminal buds average 2.5 cm in length just prior to opening and the lateral buds 1.5 to 2.0 cm. The average bud circumference ranges from 4.5 cm for the terminal and lateral buds 4.1 cm, at the first sign of petal color. Buds are oval in shape and pointed.

Sequence of development: The terminal bud on each stem will show color before any lateral bud color is visible. The flowering of the lateral buds is irregular on each stem. In the proper environments, new flower bearing shoots emerge from the sixth to eighth nodes before the terminal flower and at the base of the plant, creating a perpetual flowering plant.

Flowering response: A plant pinched 2 to 3 weeks after planting will flower 12 to 13 weeks following the pinch from a October 1 plant date and 9 to 10 weeks from a June 1 date in Fort Collins, Colo. when growing temperatures approximate 11° C. at night and 17° C. during the day.

Inflorescence type: Each initial stem is a semi-compound spray with 2 to ≡buds and 1 to 2 lateral shoots.

Number of buds and flowers per stem: Each stem has a terminal flower that develops along with the upper most, of the 2 to 4 lateral buds; new flowering shoots usually form at the sixth and seventh nodes of each initial stem resulting in an average of 4.5 flowers per stem. The lateral buds open intermittently down the stem.

Peduncle length: The length of the peduncles range from 2 mm for the top lateral bud to 3.5 cm for the lowest bud, on each stem, when the terminal flower is in prime condition.

Peduncle strength: Strong, holds flowers erect during all growing seasons; degree of brittleness is related to environmental conditions.

Flower:

*Size.*—Terminal flowers range in size from 4.6 to 5.7 cm and the laterals, 3 to 5 cm depending on the environment.

*Type.*—Commercial double with 25 to 34 moderately serrated petals, which have an average length and width of 3.6 cm and 2.2 cm, respectively.

*Form.*—Subhemispherical in longitudinal section with the petals adjacent to the calyx, slightly reflexed at maturity. Seldom splits.

Corolla color: General tonality at a distance of 1 meter: 60AB at petal margins. Upper petal surface: at margin 60A, 60B is present midway on the petal and continues to the base. Lower petal surface: extreme outer margin of 60A blending to 60B with a majority of 60C to the base.

Keeping quality: In the greenhouse, individual flower remain aesthetically pleasing up to 15 days; in the home 8 to 13 days with room temperatures of 17° C. and high, natural light intensity.

Fragrance: Slight spice fragrance which increases with temperature.

Reproductive organs:

*Androecium.*—Tyipcal carnation except has aborted 14–16 filaments, no anthers or pollen.

*Gynoecuim.*—Typical of carnation in all respects; pistil is 9 to 12 mm in length and has 2 to 3 styles and stigmas. The stigmas are light purple and change to white as the flowers mature.

Disease resistance: The plant has been found free of pathogen races currently associated with standard carnation cultivars, including the wilts and Etched Ring or Fleck viruses.

I claim:

1. A new and distinct cultivar of *Dianthus carophyllus,* Linn, identified as 85-215-6 and known as Maroon Bells and substantially as herein described and illustrated.

* * * * *

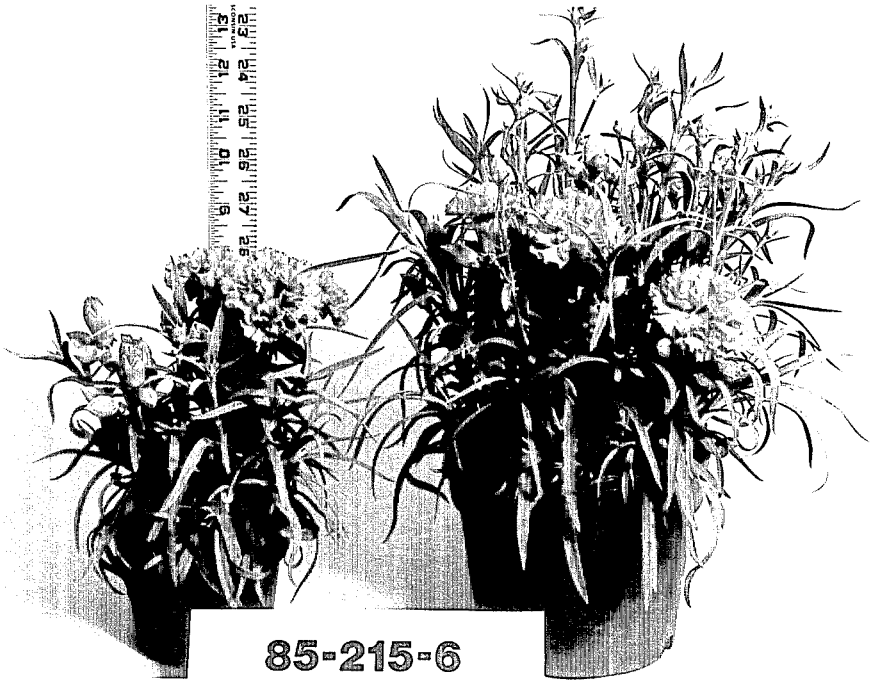
85-215-6
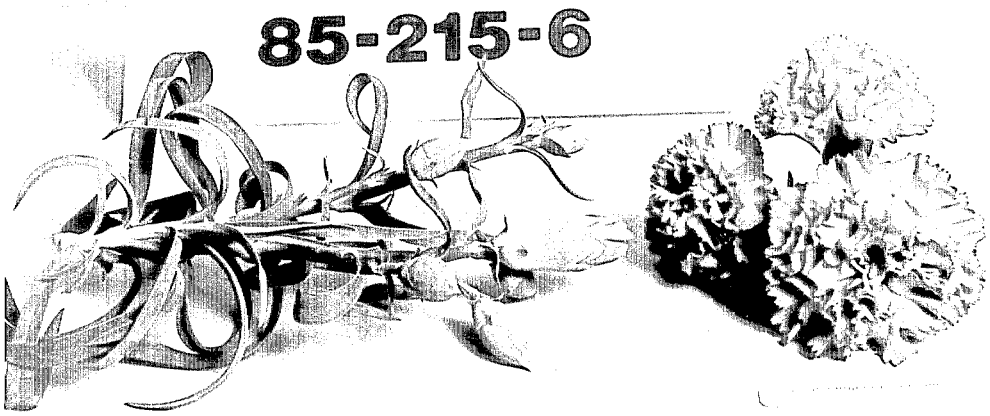
85-215-6